(12) United States Patent
Du et al.

(10) Patent No.: US 9,713,481 B2
(45) Date of Patent: *Jul. 25, 2017

(54) APPARATUS AND METHODS FOR TRANSFERRING ULTRASONIC ENERGY TO A BODILY TISSUE

(71) Applicant: Med-Sonics Corporation, Erie, PA (US)

(72) Inventors: Shu Du, Erie, PA (US); Tao Song, Erie, PA (US)

(73) Assignee: Med-Sonics Corporation, Erie, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/877,036

(22) Filed: Oct. 7, 2015

(65) Prior Publication Data

US 2016/0022306 A1 Jan. 28, 2016

Related U.S. Application Data

(63) Continuation of application No. 13/652,881, filed on Oct. 16, 2012, now Pat. No. 9,173,667.

(51) Int. Cl.
*A61B 17/32* (2006.01)
*A61B 17/22* (2006.01)
*A61B 18/00* (2006.01)

(52) U.S. Cl.
CPC ............. *A61B 17/320068* (2013.01); *A61B 17/22012* (2013.01); *A61B 2017/22015* (2013.01);
(Continued)

(58) Field of Classification Search
CPC ...... A61B 17/320068; A61B 17/22012; A61B 2017/22015; A61B 2017/22079;
(Continued)

(56) References Cited

U.S. PATENT DOCUMENTS 3,433,226 A 3/1969 Boyd
3,872,472 A 3/1975 Moschgat
(Continued)

FOREIGN PATENT DOCUMENTS

EP 0634189 A2 1/1995
EP 1025806 B1 4/2006
(Continued)

OTHER PUBLICATIONS

Office Action for U.S. Appl. No. 13/652,881, mailed May 13, 2015, 13 pages.
(Continued)

*Primary Examiner* — Theodore Stigell

(57) ABSTRACT

An apparatus includes a monolithically-constructed transmission member that defines a lumen along a longitudinal axis. The transmission member includes a first portion, a second portion, and a third portion. The first portion is configured to be coupled to an ultrasonic energy source. The second portion is configured to contact a bodily tissue to transfer ultrasonic energy from a first portion into the bodily tissue. The third portion is disposed between the first portion and the second portion and defines a cross-sectional moment of inertia that is less than at least one of a cross-sectional area moment of inertia of the first portion or a cross-sectional moment of inertia of the second portion.

20 Claims, 8 Drawing Sheets

(52) U.S. Cl.
CPC ............. *A61B 2017/22018* (2013.01); *A61B 2017/22079* (2013.01); *A61B 2017/320032* (2013.01); *A61B 2018/00577* (2013.01)

(58) Field of Classification Search
CPC A61B 2017/22018; A61B 2018/00577; A61B 2017/320032
See application file for complete search history.

(56) References Cited

U.S. PATENT DOCUMENTS

| | | | |
|---|---|---|---|
| 3,893,106 A | 7/1975 | Schulein | |
| 4,169,984 A | 10/1979 | Parisi | |
| 4,474,180 A | 10/1984 | Angulo | |
| 4,660,573 A | 4/1987 | Brumbach | |
| 4,886,491 A | 12/1989 | Parisi et al. | |
| 4,920,954 A | 5/1990 | Alliger et al. | |
| 4,933,918 A | 6/1990 | Landsrath et al. | |
| 5,358,505 A | 10/1994 | Wuchinich | |
| 5,397,301 A | 3/1995 | Pflueger et al. | |
| 5,427,118 A | 6/1995 | Nita et al. | |
| 5,447,509 A | 9/1995 | Mills et al. | |
| 5,527,273 A | 6/1996 | Manna et al. | |
| 5,540,656 A | 7/1996 | Pflueger et al. | |
| 5,562,609 A | 10/1996 | Brumbach | |
| 5,630,837 A | 5/1997 | Crowley | |
| 5,674,235 A | 10/1997 | Parisi | |
| 5,720,710 A | 2/1998 | Tachibana et al. | |
| 5,735,280 A | 4/1998 | Sherman et al. | |
| 5,746,756 A | 5/1998 | Bromfield et al. | |
| 5,827,201 A | 10/1998 | Samson et al. | |
| 5,897,569 A | 4/1999 | Kellogg et al. | |
| 5,906,628 A | 5/1999 | Miyawaki et al. | |
| 5,989,275 A | 11/1999 | Estabrook et al. | |
| 6,050,971 A | 4/2000 | Garnier | |
| 6,063,098 A | 5/2000 | Houser et al. | |
| 6,071,260 A * | 6/2000 | Halverson | A61B 17/32006 604/22 |
| 6,093,150 A | 7/2000 | Chandler et al. | |
| 6,165,163 A | 12/2000 | Chien et al. | |
| 6,217,543 B1 | 4/2001 | Anis et al. | |
| 6,274,963 B1 | 8/2001 | Estabrook et al. | |
| 6,296,620 B1 | 10/2001 | Gesswein et al. | |
| 6,299,591 B1 | 10/2001 | Banko | |
| 6,383,183 B1 | 5/2002 | Sekino et al. | |
| 6,450,975 B1 | 9/2002 | Brennan et al. | |
| 6,508,781 B1 | 1/2003 | Brennan et al. | |
| 6,511,478 B1 | 1/2003 | Burnside et al. | |
| 6,514,220 B2 | 2/2003 | Melton, Jr. et al. | |
| 6,524,299 B1 | 2/2003 | Tran et al. | |
| 6,577,042 B2 | 6/2003 | Lee et al. | |
| 6,623,444 B2 | 9/2003 | Babaev | |
| 6,689,086 B1 | 2/2004 | Nita et al. | |
| 6,743,239 B1 | 6/2004 | Kuehn et al. | |
| 6,819,027 B2 | 11/2004 | Saraf | |
| 6,866,670 B2 * | 3/2005 | Rabiner | A61B 17/00234 606/114 |
| 6,942,677 B2 | 9/2005 | Nita et al. | |
| 7,089,063 B2 | 8/2006 | Lesh et al. | |
| 7,204,820 B2 | 4/2007 | Akahoshi | |
| 7,335,169 B2 | 2/2008 | Thompson et al. | |
| 7,335,180 B2 | 2/2008 | Nita et al. | |
| 7,371,235 B2 | 5/2008 | Thompson et al. | |
| 7,431,728 B2 | 10/2008 | Gerry et al. | |
| 7,494,467 B2 | 2/2009 | Makin et al. | |
| 7,494,468 B2 | 2/2009 | Rabiner et al. | |
| 7,503,895 B2 | 3/2009 | Rabiner et al. | |
| 7,682,366 B2 | 3/2010 | Sakurai et al. | |
| 7,955,293 B2 | 6/2011 | Nita et al. | |
| 8,052,607 B2 | 11/2011 | Byrd | |
| 8,062,566 B2 | 11/2011 | Nita et al. | |
| 8,115,366 B2 | 2/2012 | Hoffman et al. | |
| 8,133,236 B2 | 3/2012 | Nita | |
| 8,152,753 B2 | 4/2012 | Nita et al. | |
| 8,182,467 B2 | 5/2012 | Nguyen et al. | |
| 8,221,343 B2 | 7/2012 | Nita et al. | |
| 8,246,643 B2 | 8/2012 | Nita | |
| 8,308,677 B2 | 11/2012 | Nita et al. | |
| 8,585,724 B2 * | 11/2013 | Palmer | A61B 10/0275 606/170 |
| 8,721,581 B2 | 5/2014 | Zolli | |
| 9,173,667 B2 * | 11/2015 | Du | A61B 17/32006 |
| 2002/0077550 A1 * | 6/2002 | Rabiner | A61B 17/22012 600/439 |
| 2002/0077643 A1 * | 6/2002 | Rabiner | A61B 17/22012 606/169 |
| 2003/0036705 A1 | 2/2003 | Hare et al. | |
| 2003/0212333 A1 | 11/2003 | Rabiner et al. | |
| 2004/0127925 A1 | 7/2004 | Du et al. | |
| 2005/0085748 A1 | 4/2005 | Culp et al. | |
| 2006/0004396 A1 | 1/2006 | Easley et al. | |
| 2006/0090956 A1 | 5/2006 | Peshknvskiy et al. | |
| 2006/0116610 A1 | 6/2006 | Hare et al. | |
| 2008/0171965 A1 | 7/2008 | Soltani et al. | |
| 2008/0294051 A1 | 11/2008 | Koshigoe et al. | |
| 2009/0018472 A1 | 1/2009 | Soltani et al. | |
| 2010/0274269 A1 | 10/2010 | Song et al. | |
| 2010/0331871 A1 | 12/2010 | Nield et al. | |
| 2011/0004149 A1 | 1/2011 | Artsyukhovich et al. | |
| 2011/0015631 A1 | 1/2011 | Wiener et al. | |
| 2011/0046522 A1 * | 2/2011 | Chan | A61B 17/22012 601/2 |
| 2011/0213397 A1 | 9/2011 | Mathonnet | |
| 2011/0301506 A1 | 12/2011 | Volz | |
| 2012/0016272 A1 | 1/2012 | Nita et al. | |
| 2012/0157890 A1 | 6/2012 | Govari et al. | |
| 2012/0163126 A1 | 6/2012 | Campbell et al. | |
| 2012/0191115 A1 | 7/2012 | Gilbert | |
| 2012/0209303 A1 | 8/2012 | Frankhouser et al. | |
| 2012/0232435 A1 | 9/2012 | Nita et al. | |
| 2013/0253387 A1 | 9/2013 | Bonutti et al. | |
| 2014/0107534 A1 | 4/2014 | Du et al. | |
| 2014/0128863 A1 | 5/2014 | Du et al. | |
| 2014/0364775 A1 | 12/2014 | Du et al. | |
| 2016/0235424 A1 | 8/2016 | Du et al. | |
| 2016/0287277 A1 | 10/2016 | Du et al. | |

FOREIGN PATENT DOCUMENTS

| | | |
|---|---|---|
| WO | WO 98/11826 | 3/1998 |
| WO | WO 99/44514 | 9/1999 |
| WO | WO 2005/072391 | 8/2005 |
| WO | WO 2006/059966 | 6/2006 |
| WO | WO2012/118018 | 9/2012 |

OTHER PUBLICATIONS

Office Action for U.S. Appl. No. 13/652,881, mailed Aug. 18, 2015, 8 pages.
International Search Report and Written Opinion for International Application No. PCT/US2013/064989, mailed May 9, 2014.
Office Action for U.S. Appl. No. 13/669,942, mailed Aug. 7, 2015, 7 pages.
"Design Considerations in Small-Diameter Medical Tubing," Jan. 1, 2001 [online] [Retrieved from the Internet] Retrieved from http://www.mddio9nline.com/print/181, Retrieved on Sep. 21, 2012.
Cyberwand™, Dual Probe Ultrasonic Lithotripter System, Cybersonics, Inc.
"Fundamentals of Ultrasonic Imaging and Flaw Detection," National Instruments tutorial, Feb. 11, 2010.
"Pebax® Tubing Grades," Applied Medical Tubing [online] [Retrieved from the Internet] Retrieved on www.appliedtubing.com/_mgxroot/page_10795.html, Retrieved on Nov. 1, 2012.
Pagnani, C. et al., "Prevention of stone migration with the Accordion during endoscopic ureteral lithotripsy," J Endourology, 26(5):484-488 (May 2012).
Extended European Search Report for EP Application No. 13847928.2, mailed Apr. 8, 2016.
Extended European Search Report for EP Application No. 13853468.0, mailed Jun. 9, 2016.

(56) References Cited

OTHER PUBLICATIONS

Office Action for U.S. Appl. No. 14/299,627, mailed Oct. 7, 2016.

\* cited by examiner

ND METHODS FOR
APPARATUS AND METHODS FOR TRANSFERRING ULTRASONIC ENERGY TO A BODILY TISSUE

This application is a continuation of U.S. patent application Ser. No. 13/652,881, now U.S. Pat. No. 9,173,667, entitled "Apparatus and Method for Transferring Ultrasonic Energy to a Bodily Tissue," filed Oct. 16, 2012, which is incorporated herein by reference in its entirety.

BACKGROUND

The embodiments described herein relate generally to a device used in conjunction with an ultrasonic ablation device and, more specifically, to a transmission member configured to transfer ultrasonic energy to a bodily tissue from an ultrasonic energy source.

Known ultrasonic energy transmission systems are used in many different medical applications, such as, for example, for medical imaging, to disrupt obstructions and/or ablate bodily tissue. In known ultrasonic energy transmission systems for tissue ablation, ultrasonic energy is transferred from an ultrasonic energy source through a transducer horn and then a transmission member, such as a wire, to a distal head. Ultrasonic energy propagates through the transmission member as a periodic wave thereby causing the distal head to vibrate. Such vibrational energy can be used to ablate or otherwise disrupt bodily tissue, for example, a vascular obstruction, a kidney stone or the like. To effectively reach various sites for treatment of intravascular occlusions or regions within the urinary tract, such ultrasonic transmission members often have lengths of about 65 cm or longer.

Known ultrasonic transmission members are constructed to be flexible enough to be passed through various bodily lumens, but also with sufficient strength to transmit ultrasonic energy to the distal tip (e.g., to ablate vascular or urinary obstructions). A stronger, more durable transmission member allows for greater transmission of energy but may not be flexible or thin enough to be advanced through the vasculature to a desired treatment area. A thinner transmission member can be more flexible but is less durable and more susceptible to breakage.

In an attempt to find a balance between strength and flexibility, some known ultrasonic transmission members are tapered along a longitudinal axis of the transmission member such that the diameter of the distal end portion decreases to allow greater flexibility. For example, some known transmission members can include a diameter at the proximal end that is greater than a diameter at a distal end. Moreover, some known transmission members can include a distal tip or "head" that is welded to the reduced diameter section, and which is positioned adjacent the tissue to be treated. Such transmission members can be prone to breakage at or near the distal end of the transmission member where the cross-sectional area of the transmission member becomes smaller and/or at the discontinuous region where the two pieces are joined. Similarly stated, such breakage is generally caused by stress concentration due to transverse vibrations and fatigue. Thus, one difficulty related to transmission of ultrasonic energy through a relatively long transmission member of known design is premature wear and breakage of the transmission member.

Furthermore, the coupling of the distal head to the distal end of the transmission member results in a discontinuity between the transmission member and the distal head due to, for example, weld material, adhesive material, or the like. Such discontinuities can produce reflections of the ultrasonic wave and result in losses of ultrasonic energy. To overcome the energy losses and inefficiency in energy transfer due to reflections or the like, some known systems increase the level of ultrasonic energy transferred through the transmission member. Similarly stated, some known systems apply a high level of energy at the proximal end portion to overcome the inefficiencies of the transmission member (e.g., at the distal end). However, the increase in the ultrasound energy transferred through the transmission member can increase stress on the transmission member and, consequently, can result in premature fatigue and breakage. In addition to the loss of transmission efficiency, known transmission members constructed of multiple pieces are expensive and can be complicated to manufacture.

Thus, a need exists for an improved apparatus and methods for transferring ultrasonic energy from an ultrasonic energy source to a bodily tissue.

SUMMARY

Devices and methods of use of a transmission device for use with an ultrasonic ablation system are described herein. In some embodiments, an apparatus includes a monolithically constructed transmission member that defines a lumen along a longitudinal axis. The transmission member includes a first portion, a second portion, and a third portion. The first portion can be coupled to an ultrasonic energy source. The second portion is configured to be disposed within the body to transfer ultrasonic energy from the first portion into the bodily tissue. The third portion is disposed between the first portion and the second portion and defines a cross-sectional moment of inertia that is less than at least one of a cross-sectional area moment of inertia of the first portion or a cross-sectional moment of inertia of the second portion.

DETAILED DESCRIPTION

Figure 1:
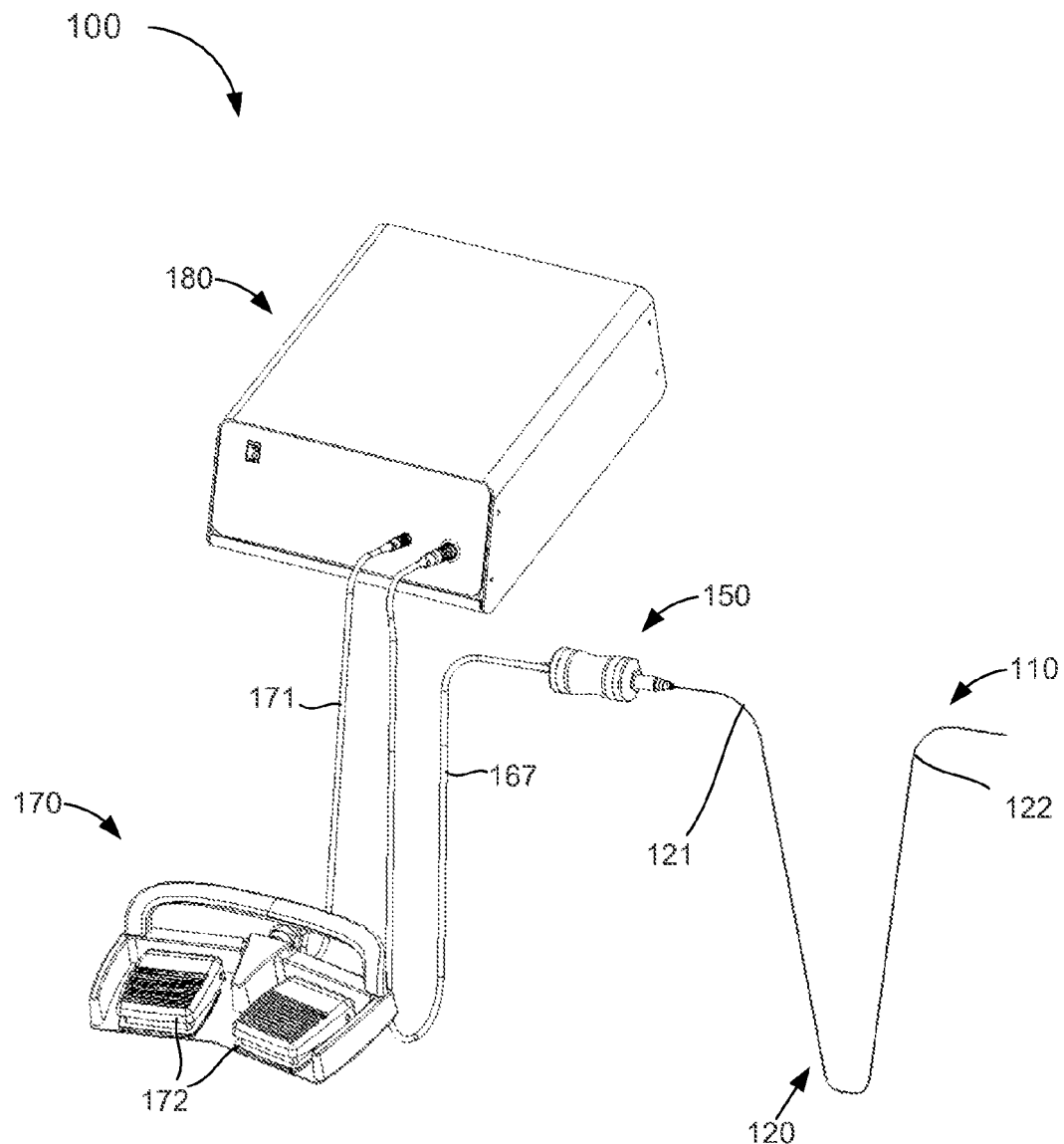
FIG. 1 is an illustration of a system for delivering ultrasonic energy to a bodily tissue according to an embodiment.

Devices and methods of use of a transmission device for use with an ultrasonic ablation system are described herein.

In some embodiments, an apparatus includes a monolithically constructed transmission member that defines a lumen along a longitudinal axis. The transmission member includes a first portion, a second portion, and a third portion. The first portion can be coupled to an ultrasonic energy source. The second portion is configured to be disposed within the body (e.g., adjacent to or in contact with a bodily tissue) to transfer ultrasonic energy from a first portion into the bodily tissue. The third portion is disposed between the first portion and the second portion and defines a cross-sectional moment of inertia that is less than at least one of a cross-sectional area moment of inertia of the first portion or a cross-sectional moment of inertia of the second portion.

In some embodiments, an apparatus includes a transmission member and an outer member coupled thereto. The transmission member includes a first end portion and a second end portion, and defines a lumen therethrough. The transmission member is configured to transfer ultrasonic energy from a first end portion to a second end portion. The transmission member further includes a sidewall that defines an elongated opening therethrough that is in fluid communication with the lumen. At least a portion of the outer member is disposed about the elongated opening of the transmission member such that the lumen is substantially fluidically isolated from a region outside of the outer member. In some embodiments, the outer member is fixedly coupled to the transmission member, for example, by a weld, an adhesive or the like. In some embodiments, the transmission member is monolithically constructed.

In some embodiments, a kit includes an ultrasonic transducer assembly and multiple transmission members each configured to be coupled to the ultrasonic transducer assembly. Each transmission member from the multiple transmission members has a diameter substantially the same as the diameter of each of the other transmission members. A first transmission member included in the multiple transmission members defines a flexural stiffness that is different than a flexural stiffness of a second transmission member included in the multiple transmission members. In some embodiments, for example, the first transmission member can define a cross-sectional area moment of inertia that is different than a cross-sectional area moment of inertia defined by the second transmission member.

In some embodiments, a method includes inserting at least a distal end portion of a monolithically constructed transmission member into a bodily lumen. The transmission member includes a proximal end portion and a flexible portion. The proximal end portion is coupled to an ultrasonic energy source. The flexible portion is disposed between the proximal end portion and the distal end portion and defines a cross-sectional area moment of inertia that is less than at least one of a cross-sectional area moment of inertia of the proximal end portion or a cross-sectional area moment of inertia of the distal end portion. The method further includes transmitting ultrasonic energy from the proximal end portion towards the distal end portion such that a portion of the ultrasonic energy is delivered to a target tissue within the bodily lumen. In some embodiments, the flexible portion can define a cross-sectional area moment of inertia that is different than a cross-sectional area moment of inertia defined by the proximal end portion and/or the distal end portion.

As used in this specification, the terms "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used herein, the term "target tissue" refers to an internal or external tissue of or within a patient to which ultrasonic energy ablation techniques are applied. For example, a target tissue can be cancer cells, tumor cells, lesions, vascular occlusions, thrombosis, calculi, uterine fibroids, bone metastases, adenomyosis, or any other bodily tissue. Furthermore, the presented examples, of target tissues are not an exhaustive list of suitable target tissues. Thus, the ultrasonic energy systems described herein are not limited to the treatment of the aforementioned tissues and can be used on any suitable bodily tissue. Moreover, a "target tissue" can also include an artificial substance within or associated with a body, such as for example, a stent, a portion of an artificial tube, a fastener within the body or the like. Thus, for example, the ultrasonic energy systems described herein can be used on or within a stent or artificial bypass graft.

As used herein, the term "stiffness" relates to an object's resistance to deflection, deformation, and/or displacement produced by an applied force, and is generally understood to be the opposite of the object's "flexibility." For example, a wall of a tube with greater stiffness is more resistant to deflection, deformation and/or displacement when exposed to a force than a wall of a tube having a lower stiffness. Similarly stated, a tube having a higher stiffness can be characterized as being more rigid than a tube having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different than the portion of the object to which the force is directly applied. Said another way, in some objects, the point of deflection is distinct from the point where force is applied.

Stiffness (and therefore, flexibility) is an extensive property of the object being described, and thus is dependent upon the material from which the object is formed as well as certain physical characteristics of the object (e.g., cross-sectional shape, length, boundary conditions, etc.). For example, the stiffness of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., nonpermanently) deform in response to an applied force. A material having a high modulus of elasticity will not deflect as much as a material having a low modulus of elasticity in the presence of an equally applied stress. Thus, the stiffness of the object can be decreased, for example, by introducing into the object and/or constructing the object of a material having a relatively low modulus of elasticity.

The stiffness of an object can also be increased or decreased by changing a physical characteristic of the object, such as the shape or cross-sectional area of the object. For example, an object having a length and a cross-sectional area may have a greater stiffness than an object having an identical length but a smaller cross-sectional area. As another example, the stiffness of an object can be reduced by including one or more stress concentration risers (or discontinuous boundaries) that cause deformation to occur under a lower stress and/or at a particular location of the object. Thus, the stiffness of the object can be decreased by decreasing and/or changing the shape of the object.

The stiffness (or inversely, the flexibility) of an elongated object, such as a catheter or tube can be characterized by its flexural stiffness. The flexural stiffness of an object can be used to characterize the ease with which the object deflects under a given force (e.g., the ease with which the object deflects when the object is moved along a tortuous path within the body). The flexural stiffness of an object, such as a catheter, transmission member or the like, can be mathematically expressed as shown below:

$$k = \frac{3EI}{L^3}$$

where k is the flexural stiffness of the object, E is the modulus of elasticity of the material from which the object is constructed, I is the area moment of inertia of the object (defined below), and L is the length of the object.

As used herein, the terms "cross-sectional area moment of inertia," "area moment of inertia," and/or "second moment of area" relate to an object's resistance to deflection or displacement around an axis that lies in a cross-sectional plane. The area moment of inertia is dependent on the cross-sectional area and/or shape of the object and can be mathematically expressed as a function of a cross-section of the object. The area moment of inertia of an object (e.g., such as the tubes disclosed herein) is described having units of length to the fourth power (e.g., in$^4$, mm$^4$, cm$^4$, etc.). In this manner, the "area moment of inertia" is differentiated from the "moment of inertia" or "mass moment of inertia" which is expressed having units of mass times units of length to the second power (e.g., kg*m$^2$, lb$_m$*ft$^2$, etc.).

Two mathematical formulas are used herein to define an area moment of inertia for a substantially annular cross-sectional shape and for a substantially arc-shaped cross-sectional shape. The area moment of inertia for the annular cross-section shape is expressed below as:

$$I = \frac{\pi(d_o^4 - d_i^4)}{64}$$

where $d_o$ is an outside diameter of the annulus and $d_i$ is an inner diameter of the annulus.

The area moment of inertia for an arced cross-sectional shape is expressed below as:

$$I = \frac{r^3 t}{2}[\alpha + \cos(\alpha - \frac{\pi}{2})]$$

where r is the radius of the arc, t is the thickness of the arc segment (e.g., $d_o$–$d_i$), and α is the subtended angle of the radius. For continuity with the area moment of inertia equation for the annular cross-section, the equation can be expressed as shown below:

$$I = \frac{d_i^3(d_o - d_i)}{16}[\alpha + \cos(\alpha - \frac{\pi}{2})]$$

Embodiments described herein relate to ultrasonic energy ablation systems. In such systems a transmission member can be operably coupled to an ultrasonic energy source to deliver ultrasonic energy to a target bodily tissue. For example, FIG. 1 is an illustration of an ultrasonic energy ablation system 100, according to an embodiment. The ultrasonic energy ablation system 100 (also referred to herein as "ultrasonic system" or simply "system") includes an ultrasonic generator 180, a foot switch 170, an ultrasonic transducer assembly 150, and a probe assembly 110. The ultrasonic generator 180 (or "generator") can be any suitable generator configured to generate, control, amplify, and/or transfer an electric signal (e.g., a voltage) to the transducer assembly 150.

The ultrasonic generator 180 includes at least a processor, a memory and the circuitry (not shown in FIG. 1) to produce an electronic signal (i.e., a current and a voltage) having the desired characteristics that can be received by the ultrasonic transducer assembly 150 and converted into ultrasonic energy. In some embodiments, the ultrasonic generator 180 can be electrically coupled to (e.g., "plugged into") an electric receptacle such that the ultrasonic generator 180 receives a flow of electric current. For example, in some embodiments, the ultrasonic generator 180 can be plugged into a wall outlet that delivers alternating current (AC) electrical power at a given voltage (e.g., 120V, 230V, or other suitable voltage) and a given frequency (e.g., 60 Hz, 50 Hz, or other suitable frequency).

Although not shown in FIG. 1, the ultrasonic generator 180 includes the electronic circuitry, hardware, firmware and or instructions to cause the ultrasonic generator 180 to act as a frequency inverter and/or voltage booster. In this manner, the ultrasonic generator 180 can produce and/or output a voltage to the transducer assembly 150 having the desired characteristics to produce the desired ultrasonic energy output. For example, in some embodiments, the ultrasonic generator 180 can receive AC electrical power at a frequency of approximately 60 Hz and a voltage of approximately 120V and convert the voltage to a frequency up to approximately 20,000 Hz to 35,000 Hz with a voltage of approximately 500-1500 VAC (RMS). Thus, the ultrasonic generator 180 can supply the transducer assembly 150 with a flow of AC electrical power having an ultrasonic frequency.

As shown in FIG. 1, the system 100 includes the foot switch 170 that is in electric communication with the ultrasonic generator 180 via a foot switch cable 171. The foot switch 170 includes a set of pedals 172 (e.g., two pedals as shown) that are operative in controlling the delivery of the ultrasonic electrical energy supplied to the ultrasonic transducer assembly 150. For example, in some embodiments, a user (e.g., a physician, technician, etc.) can engage and/or depress one or more of the pedals 172 to control the current supplied to the ultrasonic transducer assembly 150 such that, in turn, the probe assembly 110 delivers the desired ultrasonic energy to the bodily tissue, as further described in detail herein.

The transducer assembly 150 is in electric communication with the ultrasonic generator 180 via a transducer cable 167. In this manner, the transducer assembly 150 can receive an electrical signal (i.e., voltage and current) from the ultrasonic generator 180. The transducer assembly 150 is configured to produce and amplify the desired ultrasonic energy via a set of piezoelectric members 162 (i.e., piezoelectric rings) and an ultrasonic horn 163 (see e.g., FIG. 2), and transfer the ultrasonic energy to the probe assembly 110 and/or the transmission member 120. The transducer assembly 150 can be any suitable assembly of the types shown and described herein.

Figure 2:
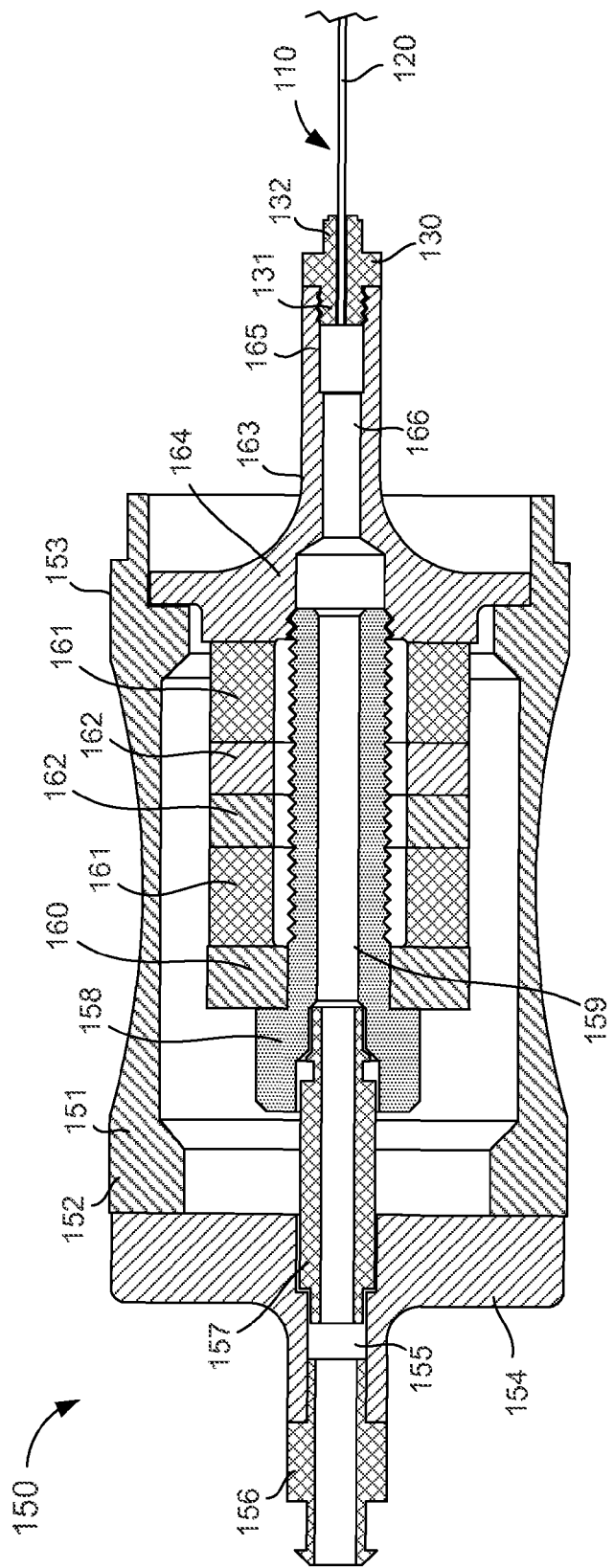
FIG. 2 is a cross-sectional view of an ultrasonic transducer included in the system of FIG. 1.

For example, in some embodiments, as shown in FIG. 2, the transducer assembly 150 includes a housing 151 having a proximal end portion 152 and a distal end portion 153. The housing 151 is configured to house or otherwise enclose at least a portion of a flow tube 157, a bolt 158, a back plate 160, a set of insulators 161, a set of piezoelectric rings 162, and a transducer horn 163.

The proximal end portion 152 of the housing 151 is coupled to a proximal cover 154 (e.g., via an adhesive, a press or friction fit, a threaded coupling, a mechanical fastener, or the like). The proximal cover 154 defines an opening 155 such that the proximal cover 154 can receive a portion of a connector 156 (e.g., a luer connector) on a proximal side thereof (e.g., substantially outside the housing 151) and a portion of the flow tube 157 on a distal side thereof (e.g., substantially inside the housing 151). Expanding further, the proximal cover 154 can receive the connector 156 and the flow tube 157 such that the proximal cover 154 forms a substantially fluid tight seal with the connector 156 and the flow tube 157. In this manner, a vacuum can be applied via the connector 156 to irrigate and/or aspirate the region of the body within which the probe assembly 110 is disposed. Similarly stated, this arrangement results in the connector 156 being placed in fluid communication with the lumen 122 defined by the transmission member 120.

The distal end portion 153 of the housing 151 is configured to receive the transducer horn 163 such that the transducer horn 163 is coupled to an inner surface of the housing 151. More specifically, the transducer horn 163 can be disposed at least partially within the housing 151 such that the transducer horn 163 can be moved relative to the housing 151 (e.g., when amplifying the ultrasonic energy), but not moved out of the housing 151 during normal use. The transducer horn 163 includes a proximal end portion 164 and a distal end portion 165 and defines a lumen 166 therethrough. The lumen 166 is configured to receive a portion of the bolt 158 at the proximal end portion 164 of the transducer horn 163 and a portion of the probe assembly 120 at the distal end portion 165 of the transducer horn 163, both of which are described in further detail herein.

As shown in FIG. 2, the back plate 160, the insulators 161, and the piezoelectric rings 162 are disposed within the housing 151 and about the bolt 158. More specifically, the arrangement of the back plate 160, the insulators 161, and the piezoelectric rings 162 is such that the back plate 160 is disposed proximal to the insulators 161 and the piezoelectric rings 162. The piezoelectric rings 162 are each disposed between the insulators 161. Similarly stated, a first insulator 161 is disposed proximal to the piezoelectric rings 162 and a second insulator 161 is disposed distal to the piezoelectric rings 162. The piezoelectric rings 162 are in electric communication (e.g., via wires not shown in FIGS. 1 and 2) with the ultrasonic generator 180, as described in further detail herein.

As shown in FIG. 2, a portion of the bolt 158 is configured to be disposed within the lumen 166 defined by the transducer horn 163. More specifically, the portion of the bolt 158 forms a threaded fit with an inner surface of the transducer horn 163 that defines the lumen 166. In this manner, the bolt 158 can be advanced within the lumen 166 such that the bolt 158 exerts a compressive force on the backing plate 160, the insulators 161, and the piezoelectric rings 162. Thus, the backing plate 160, the insulators 161, and the piezoelectric rings 162 are retained between a head of the bolt 158 (e.g., at the proximal end) and a proximal surface of the transducer horn 163. The torque applied to the bolt and/or the clamping force exerted between the head of the bolt 158 and the proximal surface of the transducer horn 163 is such that that the deviation of the transducer natural frequency deviation is within ten percent from nominal. Therefore, in use, the piezoelectric rings 162 can vibrate and/or move the transducer horn 163, as further described herein.

The bolt 158 further defines a lumen 159 such that a proximal end portion of the bolt 158 can receive a distal end portion of the flow tube 157. In this manner, the lumen 159 defined by the bolt 158 and the flow tube 157 collectively place the lumen 166 defined by the transducer horn 163 in fluid communication with the connector 156. Thus, the lumen 166 of the transducer horn 163 can be placed in fluid communication with a volume substantially outside of the proximal end of the housing 151.

As shown in FIGS. 1 and 2, the probe assembly 110 includes at least a transmission member 120 and a coupler 130. The coupler 130 includes a proximal end portion 131 and a distal end portion 132 and defines a lumen 133 that extends therethrough. The proximal end portion 131 of the coupler 130 is disposed within the lumen 166 at the distal end portion 165 of the transducer horn 163 and forms a threaded fit with the inner surface of the transducer horn 163 that defines the lumen 166. The distal end portion 131 of the coupler 130 is configured to receive a portion of the transmission member 120 to fixedly couple the transmission member 120 to the coupler 130. In this manner, the probe assembly 110 can be removably coupled to the transducer assembly 150 via the coupler.

The transmission member 120 is an elongate tube having a proximal end portion 121 and a distal end portion 122. The transmission member 120 can be any suitable shape, size, or configuration and is described in further detail herein with respect to specific embodiments. In some embodiments, the transmission member 120 can optionally include any suitable feature configured to increase the flexibility (e.g., decrease the stiffness) of at least a portion of the transmission member 120, thereby facilitating the passage of the transmission member 120 through a tortuous lumen within a patient (e.g., a urinary tract, a vein, artery, etc.). For example, in some embodiments, a portion of the transmission member 120 can be formed from a material of lower stiffness than a different portion of the transmission member 120 formed from a material of greater stiffness. In some embodiments, the stiffness of at least a portion of the transmission member 120 can be reduced by defining an opening (e.g., notch, a groove, a channel, a cutout, or the like), thereby reducing the area moment of inertia of the portion of the transmission member 120, as described herein with respect to specific embodiments.

In use, a user (e.g., a surgeon, a technician, physician, etc.) can operate the ultrasonic system 100 to deliver ultrasonic energy to a target bodily tissue within a patient. The user can, for example, engage the pedals 172 of the foot switch 170 such that the ultrasonic generator 180 generates an alternating current (AC) and voltage with a desired ultrasonic frequency (e.g., 20,000 Hz). In this manner, the ultrasonic generator 180 can supply AC electric power to the piezoelectric rings 162. The AC electric power can urge the piezoelectric rings 162 to oscillate (e.g., expand, contract, or otherwise deform) at the desired frequency, which, in turn, causes the transducer horn 163 to move relative to the housing 151. Thus, with the probe assembly 110 coupled to the transducer horn 163, the movement of the transducer horn 163 vibrates and/or moves the probe assembly 110. In this manner, the distal end portion 122 of the transmission member 120 can be disposed with a portion of the patient adjacent to a target tissue such that the transmission member 120 transfers at least a portion of the ultrasonic energy to the target tissue (not shown in FIGS. 1 and 2). For example, in some embodiments, a distal tip of the transmission member 120 can impact a target tissue such as, for example, to break apart the occlusion. In some embodiments, the movement of the distal end portion 122 of the transmission member 120 is such that cavitations occur within the portion of the patient. In this manner, the cavitations can further break apart a target tissue. In some embodiments, the ultrasonic system 100 can optionally be used to aspirate and/or to supply irrigation to a target tissue site.

Figure 3:
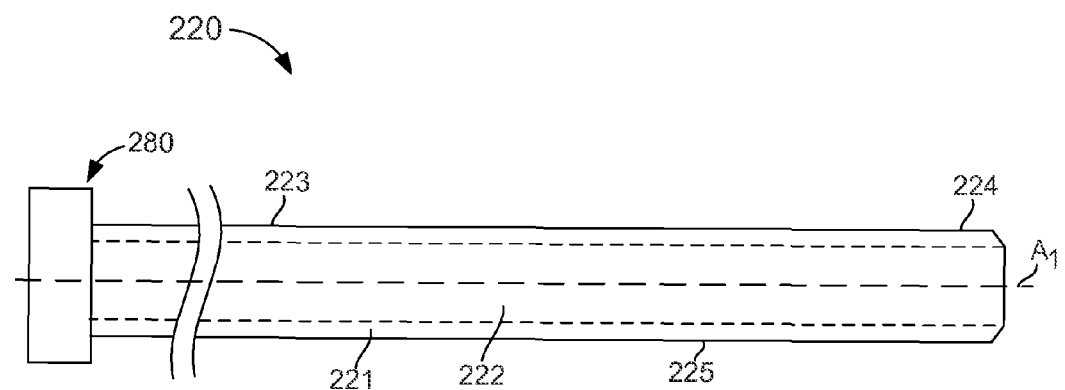
FIG. 3 is a schematic illustration of a transmission member, according to an embodiment.

While described above in a general way, an ultrasonic energy system, such as the ultrasonic energy system 100, can include any suitable probe or transmission member of the types shown herein having increased flexibility to facilitate the passage of the transmission member through a tortuous lumen within a patient. For example, in some embodiments, a transmission member can have a suitable flexibility such that at least a portion of the transmission member can elastically (e.g., not permanently) deform within the tortuous anatomical structure. For example, FIG. 3 is a schematic illustration of a transmission member 220, according to an embodiment. The transmission member 220 can be included in any suitable ultrasonic energy system shown and described herein, such as, for example, the system 100 described above with reference to FIGS. 1 and 2. The transmission member 220 is a monolithically-constructed elongate member including a side wall 221 and defining a lumen 222 along a longitudinal axis $A_1$. In this manner, the transmission member 220 can provide aspiration from and/or irrigation (via the lumen 222, and the connecting lumens of any component to which the transmission member 220 is coupled) to a target tissue site during an ultrasonic procedure.

As shown in FIG. 3, the transmission member 220 includes a first portion 223, a second portion 224, and a third portion 225. The first portion 223 can be, for example, a proximal end portion, and can be at least operably coupled to an ultrasonic energy source 280, such as for example, the ultrasonic generator 180 and/or the transducer assembly 150 described above. For example, in some embodiments, the first portion 223 can be disposed within a lumen of a coupler member (not shown), as described above with reference to FIG. 2. In such embodiments, the coupler member can be coupled to the ultrasonic energy source 280, thus, operably coupling the transmission member 220 to the ultrasonic energy source 280. The second portion 224 can be, for example, a distal end portion of the transmission member 220, and can be disposed within a body (not shown) to transfer ultrasonic energy from the first portion 223 into a bodily tissue.

The third portion 225 is disposed between the first portion 223 and the second portion 224. The third portion 225 defines a cross-sectional area moment of inertia that is less than a cross-sectional area moment of inertia of the first portion 223 and/or the second portion 224. In this manner, the transmission member 220 has a suitable flexural stiffness to be disposed along and/or within a tortuous path within the body such that the transmission member 220 efficiently and reliably transmits ultrasonic energy from the first portion 223 to the second portion 224. More particularly, the lower area moment of inertia of third portion 225 allows the third portion 225 to elastically deform more easily than the first portion 223 and/or the second portion 224. Said another way, the third portion 225 can bend (e.g., elastically) more easily about an axis that is perpendicular to the longitudinal axis $A_1$ of the transmission member 220 than can the first portion 223 and/or the second portion 224.

Moreover, the greater flexural stiffness of the first portion 223 and/or the second portion 224 can reduce losses of ultrasonic energy transmitted through the transmission member 220 that are associated with more flexible materials and/or members. Similarly stated, the spatial variation in the area moment of inertia results higher transmission efficiency than would otherwise be obtained when forming the transmission member 220 to have a constant, lower flexural stiffness. Because the transmission member 220 is monolithically constructed, it is devoid of material interfaces that are known to cause reflection of the ultrasonic energy waves (and thereby inefficient transfer of the same). Additionally, because the transmission member 220 is monolithically constructed, there is a reduced likelihood that the transmission member 220 will fail during use as a result of discontinuities and/or stress concentration risers associated with the joining of separately constructed pieces.

The transmission member 220 can be formed from any suitable material such as, for example, Type 304 stainless steel, Type 316 stainless steel, nickel titanium alloy (nitinol), or any other super elastic metal or metal alloy. In some embodiments, the first portion 223, the second portion 224, and/or the third portion 225 can be formed from a material that is dissimilar from the material of the other portions. For example, in some embodiments, the first portion 223 and the second portion 224 can be formed from a first material and the third portion 225 can be formed from a second material. In such embodiments, the first material can have a modulus of elasticity that is substantially greater than the modulus of elasticity of the second material. For example, in some embodiments, the first portion 223 and the second portion 224 can be formed from Type 304 stainless steel and the third portion 225 can be formed from nitinol. In this manner, the first portion 223 and the second portion 224 can have a higher rigidity than that of the third portion 225. Similarly stated, the third portion 225 can have a lower flexural stiffness (defined above) than the flexural stiffness of the first portion 223 and the second portion 224.

In other embodiments, the monolithically-formed transmission member 220 can be formed from a substantially uniform material (e.g., a single material). Similarly stated, in some embodiments, the flexural stiffness of the first portion 223 and the second portion 224 can be greater than the flexural stiffness of the third portion 225 while being formed from the same material. In such embodiments, the spatial variation in the area moment of inertia is achieved by varying the cross-sectional size and/or shape of the transmission member 220 along its longitudinal axis $A_1$. For example, in some embodiments, the transmission member 220 can be substantially cylindrical and can have a uniform outer diameter along a length of the transmission member 220. Similarly stated, the first portion 223, the second portion 224, and the third portion 225 can each have substantially the same outer diameters. In such embodiments, the first portion 223, the second portion 224, and the third portion 225 can have a dissimilar inner diameter. For example, the first portion 223 and/or the second portion 224 can have an inner diameter that is smaller (resulting in a thicker sidewall 221) than the inner diameter of the third portion 225. Thus, the first portion 223 and/or the second portion 224 have an area moment of inertia that is greater than the area moment of inertia of the third portion 225. In this manner, the first portion 223 and/or the second portion 224 have a flexural stiffness that is greater than the flexural stiffness of the third portion 225.

In other embodiments, the outer diameter of the first portion 223 and/or the outer diameter of the second portion 224 can be greater than the outer diameter of the third portion 225. Thus, by maintaining a similar inner diameter, the first portion 223 and/or the second portion 224 can have a greater area moment of inertia than the area moment of inertia of the third portion 225. In this manner, the first portion 223 and/or the second portion 224 have a flexural stiffness greater than the flexural stiffness of the third portion 225.

Figure 4:
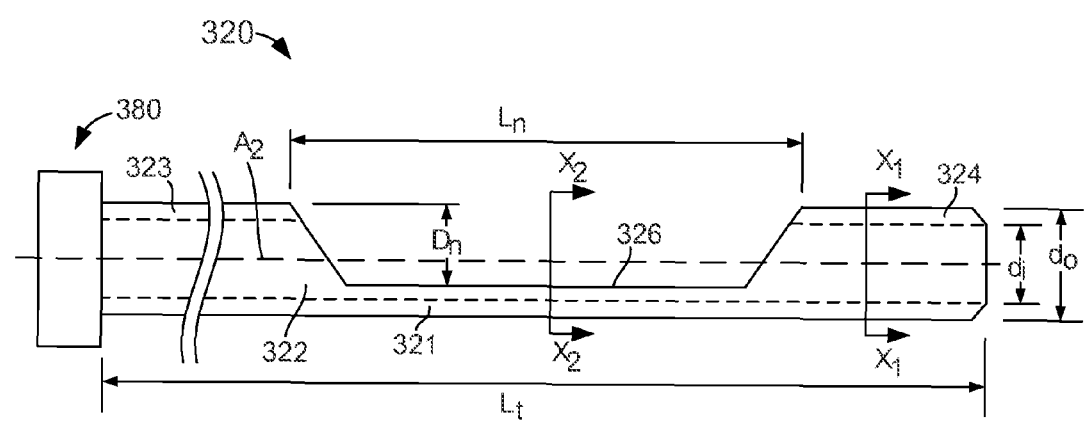
FIG. 4 is an illustration of a transmission member, according to an embodiment.
Figure 5:
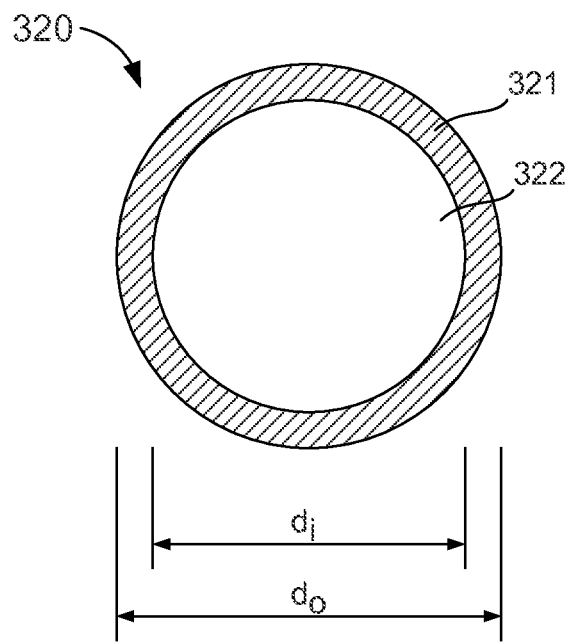
FIG. 5 is a cross-sectional view of the transmission member of FIG. 4 taken along the line $X_1$-$X_1$.
Figure 6:
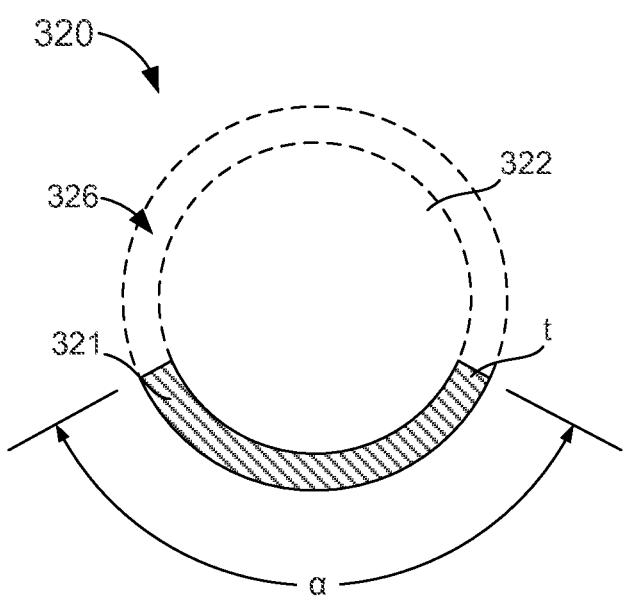
FIG. 6 is a cross-sectional view of the transmission member of FIG. 4 taken along the line $X_2$-$X_2$.

In yet other embodiments, the nominal outer diameter and the nominal inner diameter of the transmission member can be substantially constant. In such embodiments, a portion of a transmission member can include and/or define a discontinuity or change in cross-sectional shape configured to reduce the area moment of inertia of at least the portion of the transmission member. For example, FIGS. 4-6 are schematic illustrations of a transmission member 320, according to an embodiment. The transmission member 320 can be included in any suitable ultrasonic energy system such as, for example, the system 100 described above with reference to FIGS. 1 and 2. The transmission member 320 is a monolithically-constructed elongate member including a side wall 321 and defining a lumen 322 along a longitudinal axis $A_2$. In this manner, the transmission member 320 can provide aspiration from and/or irrigation (via the lumen 322) to a target tissue site during an ultrasonic procedure.

The transmission member 320 includes a first portion 323 and a second portion 324. The first portion 323 can be, for example, a proximal end portion and can be at least operably coupled to an ultrasonic energy source 380, such as for example, the ultrasonic generator 180 and/or the transducer assembly 150 described above. For example, in some embodiments, the first portion 323 can be disposed within a lumen of a coupler member (not shown), as described above with reference to FIG. 2. In such embodiments, the coupler member can be coupled to the ultrasonic energy source 380, thus, operably coupling the transmission member 220 to the ultrasonic energy source 380. The second portion 324 can be, for example, a distal end portion of the transmission member 320, and can be disposed within a body (not shown) to transfer ultrasonic energy from the first portion 223 into a bodily tissue.

The transmission member 320 can be substantially cylindrical and can have a uniform outer diameter $d_o$ along a length $L_t$ of the transmission member 320. The walls 321 of the transmission member 321 can be configured such that the transmission member 320 also has a substantially uniform inner diameter $d_i$. Similarly stated, the first portion 323 and the second portion 324 can each have substantially the same outer diameters and substantially the same inner diameters.

The transmission member 320 can be any suitable size. For example, in some embodiments, the walls 321 have a thickness t of approximately 0.006 inches, the outer diameter $d_o$ is approximately 0.032 inches, and the inner diameter $d_i$ is approximately 0.020 inches. In other embodiments, the outer diameter $d_o$ of the transmission member 320 can be between approximately 0.014 and 0.050 inches and the inner diameter $d_i$ can be between approximately 0.010 and 0.040 inches. In some embodiments, the length $L_t$ of the transmission member 320 is approximately 57.5 inches.

The transmission member 320 further defines an elongate opening 326 (e.g., a notch, a groove, a channel, a cutout, etc.) along at least a portion of the longitudinal axis $A_2$ that is in fluid communication with the lumen 322. The opening 326 can be any suitable shape, size, or configuration. For example, as shown in FIG. 4, the opening 326 can be substantially symmetrical relative to a plane perpendicular to the longitudinal axis $A_2$. Moreover, the transmission member 320 can be configured such that the elongate opening 326 has a desired length $L_n$ and a desired depth $D_n$. For example, in some embodiments, the length $L_n$ of the opening 326 can be approximately 5 times the outer diameter $d_o$ of the transmission member. In other embodiments, the length $L_n$ of the opening 326 can be greater than 5 times the outer diameter $d_o$ of the transmission member. In still other embodiments, the length $L_n$ of the opening 326 can be related to the length $L_t$ of the transmission member 320. For example, in some embodiments, the length $L_n$ of the opening 326 can be between 40 percent and 90 percent of the length $L_t$ of the transmission member 320.

The depth $D_n$ of the opening 326 can be, for example, at least half of the outer diameter $d_o$ of the transmission member 320 (resulting in a subtended angle, as described below, of approximately 180 degrees). In other embodiments, the depth $D_n$ of the opening 326 can be approximately 0.016 inches. In other embodiments, the depth $D_n$ of the opening 326 can be between approximately 0.2 to 0.8 times the outer diameter $d_o$ of the transmission member 320.

As shown in FIGS. 5 and 6, the cross-sectional shape of the transmission member 320 is substantially changed at positions along the longitudinal axis $A_2$. More specifically, FIG. 5 illustrates a cross-sectional shape of the transmission member 320 taken at a location along the longitudinal axis $A_2$ away from a region of the opening 326, and FIG. 6 illustrates a substantially arced cross-sectional shape of the transmission member 320 taken at a location along the longitudinal axis $A_2$ that includes the opening 326. As shown in FIG. 6, the presence of the opening 326 results in the transmission member 320 having an arc-shaped cross-sectional shape along a portion thereof. The transmission member 320 can be configured such that the arced cross-sectional shape has a subtended angle α of between approximately 20 degrees and approximately 120 degrees. In other embodiments, the transmission member 320 is configured such that the arced cross-sectional shape has a subtended angle α of up to approximately 180 degrees.

The opening 326 can be such that the transmission member 320 has an area moment of inertia at a position along the longitudinal axis $A_2$ having the arced cross-sectional shape that is substantially less than an area moment of inertia at a position along the longitudinal axis $A_2$ having the annular cross-sectional shape. In this manner, the flexural stiffness of the transmission member 320 at a position having the arced cross-sectional shape is substantially less than the flexural stiffness of the transmission member 320 at a position having the annular cross-sectional shape. Furthermore, because the walls 321 have a substantially uniform thickness t, the flexibility of at least a portion of the transmission member 320 can be increased while substantially limiting the loss of stiffness in the axial direction.

The lower area moment of inertia of transmission member 320 at a portion of the transmission member 320 having the arced cross-sectional shape allows the portion to elastically deform more than a portion of the transmission member 320 having a greater area moment of inertia (e.g., having the annular cross-sectional shape). More specifically, the portion having the arced cross-sectional shape can bend (e.g., elastically) about an axis that is perpendicular to the longitudinal axis $A_2$ of the transmission member 320 without kinking, breaking, or otherwise plastically deforming.

The lower flexural stiffness of the transmission member 320 can allow at least the portion of the transmission member 320 having the arced cross-sectional shape to elastically deform a desired amount while being passed through a tortuous anatomical structure (e.g., a urinary tract, vein or artery), thereby reducing patient discomfort. Moreover, the portions of the transmission member 320 with the arced cross-sectional shape can retain a sufficient stiffness in the axial direction to substantially limit losses of ultrasonic energy transmitted through the transmission member 320 that would otherwise be lost due to forming the transmission member 320 from a material having a lower stiffness. In addition, the transmission member 320 can be configured such that the opening 326 is disposed at a suitable distance from a distal end of the transmission member 320. Thus, the outer diameter $d_o$ of the transmission member 320 can be sufficiently large such that a distal tip of transmission member 320 can deliver ultrasonic energy to a target tissue.

Although not shown in FIGS. 4-6, in some embodiments, a transmission member can be at least partially disposed within an outer member of a probe assembly. For example, in some embodiments, a probe assembly can include an outer member configured to substantially circumscribe the transmission member. In such embodiments, the outer member can be, for example, a catheter or sheath fixedly coupled to the transmission member via an adhesive. In this manner, the outer member can be configured to retain the transmission member within a set of walls (e.g., within a lumen defined by the set of walls) in the event of breakage, thereby limiting the risk of a portion of the transmission member being lost within a portion of the patient.

Figure 7:
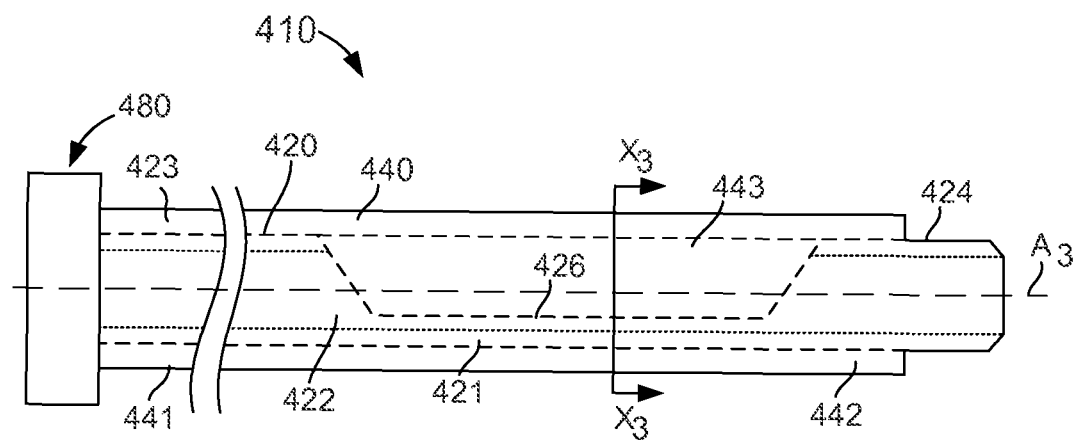
FIG. 7 is an illustration of a probe assembly according to an embodiment.
Figure 8:
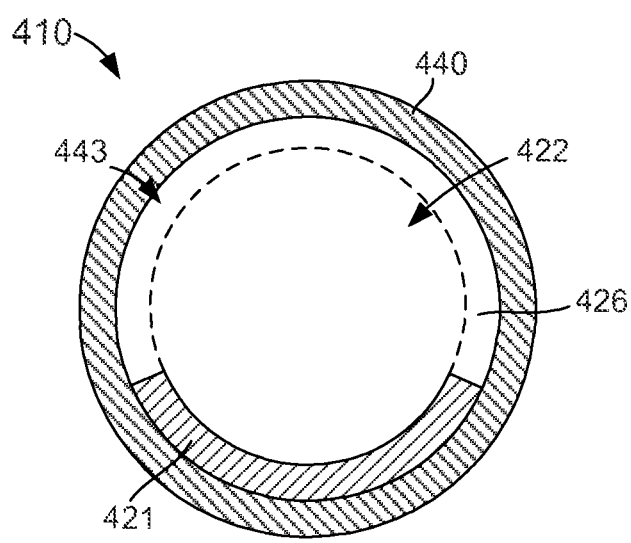
FIG. 8 is a cross-sectional view of the probe assembly of FIG. 7 taken along the like $X_3$-$X_3$.

For example, FIGS. 7 and 8 are schematic illustrations of a probe assembly 410, according to an embodiment. The probe assembly 410 includes a transmission member 420 and an outer member 440. The probe assembly 410 can be included in any suitable ultrasonic energy system such as, for example, the system 100 described above with reference to FIGS. 1 and 2. The transmission member 420 includes a side wall 421 and defines a lumen 422 along a longitudinal axis $A_3$. In this manner, the transmission member 420 can provide aspiration from and/or irrigation (via the lumen 422) to a target tissue site during an ultrasonic procedure, as further described below.

The transmission member 420 includes a first portion 423 and a second portion 424. The first portion 423 can be, for example, a proximal end portion, and can be at least operably coupled to an ultrasonic energy source 480, such as for example, the ultrasonic generator 180 and/or the transducer assembly 150 described above. For example, in some embodiments, the first portion 423 can be disposed within a lumen of a coupler member (not shown), as described above with reference to FIG. 2. In such embodiments, the coupler member can be coupled to the ultrasonic energy source 480, thus, operably coupling the transmission member 420 to the ultrasonic energy source 480. The second portion 424 can be, for example, a distal end portion of the transmission member 420, and can be disposed within a body (not shown) to transfer ultrasonic energy from the first end portion 423 into a bodily tissue.

The transmission member 420 defines an elongate opening 426 (e.g., a notch, a groove, a channel, a cutout, etc.) along at least a portion of the longitudinal axis $A_3$ that is in fluid communication with the lumen 422. The opening 426 can be any suitable shape, size, or configuration. The transmission member 420 can be substantially similar to the transmission member 320 described above with reference to FIGS. 4-6. Therefore, the transmission member 420 is not described in further detail herein.

The outer member 440 includes a proximal end portion 441 and a distal end portion 442 and defines a lumen 443 therethrough. The proximal end portion 441 can be configured to be disposed adjacent a coupler member. The distal end portion 442 can be disposed adjacent a distal tip of the transmission member 420. More specifically, the distal end portion 442 can be disposed a desired distance from the distal tip of the transmission member 420 such that the outer member 440 does not substantially dampen and/or otherwise interfere with the vibration and/or movement of the distal tip of the transmission member 420 and/or the transmission of the ultrasonic energy therethrough. In some embodiments, the outer member 440 is disposed from the distal end tip by approximately 0.050 to 0.150 inches.

The outer member 440 is coupled to the transmission member 420 such that a portion of the outer member 440 is disposed about the elongate opening 426. In this manner, the lumen 422 is maintained in fluid isolation from a region outside of the transmission member 420. Thus, the lumen 422 can be used to aspirate and/or irrigate a target tissue site disposed adjacent the distal tip of the transmission member 420 during an ultrasonic procedure. More specifically, the ultrasonic energy source 480 can supply ultrasonic energy through the transmission member 420 to a target tissue and the ultrasonic energy source 480 (or other device) can be configured to simultaneously aspirate and/or irrigate the target tissue site via the lumen 422. In addition to maintaining fluid isolation of the lumen 422, the outer member 440 also circumscribes the transmission member 420 to maintain any portions thereof that may result in the event of a failure. Similarly stated, in some embodiments, the outer member 440 can be fixedly coupled to the transmission member 420 such that if a portion of the transmission member 420 breaks, it will be retained within the outer member 440.

In some embodiments, the outer member 440 is fixedly coupled to the transmission member 420. For example, in some embodiments, the outer member 440 can be fixedly coupled to the transmission member 420 via an adhesive, a friction fit, a threaded coupling, or any other suitable coupling method. The outer member 440 can be any suitable member configured to substantially circumscribe the transmission member 420. For example, in some embodiments, the outer member 440 can be a catheter. In other embodiments, the outer member 440 can be formed from multiple layers of material having any given properties. For example, in some embodiments, the outer member 440 can be formed with an outer layer that can be polytetrafluoroethylene (PTFE). In other embodiments, the outer layer can include a hydrophobic coating or a hydrophilic coating. In some embodiments, the outer member 440 can include an inner layer configured to enhance the adhesion properties of the outer member 440 to facilitate the coupling of the outer member 440 to the transmission member 420. Moreover, the arrangement of the outer member 440 is such that the outer member 440 does not limit the desired flexibility of the transmission member 420 disposed therein. Similarly stated, the outer member 420 can be sufficiently flexible to allow the transmission member 420 to deflect within a bodily lumen, as described above.

Figure 9:
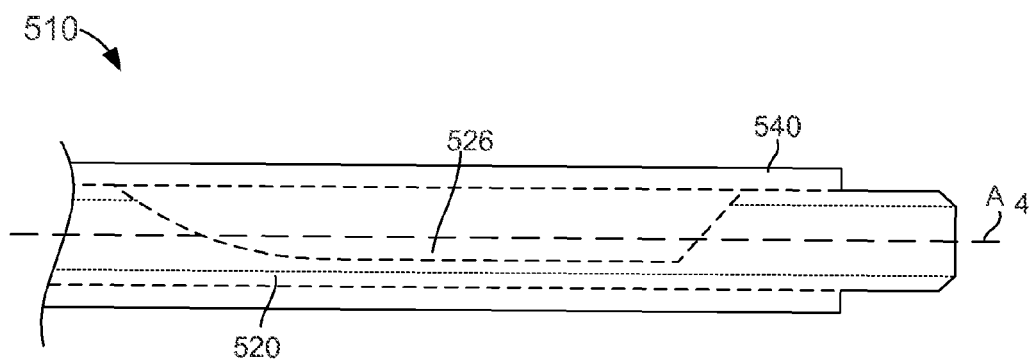
FIG. 9 is a schematic illustration of a probe assembly according to an embodiment.

While the transmission member 420 is shown in FIG. 7 as having an opening that is substantially symmetrical about a plane perpendicular to the longitudinal axis $A_3$, in some embodiments, a transmission member can include an opening that is substantially asymmetrical. For example, FIG. 9 is an illustration of a probe assembly 510, according to an embodiment. The probe assembly 510 includes a transmission member 520, defining an elongate opening 526, and an outer member 540. The transmission member 520 and the outer member 540 can be substantially similar in form and function to the transmission member 420 and the outer member 440, respectively, described with reference to FIGS. 7 and 8. Thus, the transmission member 520 and the outer member 540 are not described in further detail herein. The transmission member 520 differs from the transmission member 420, however, in the arrangement of the opening 526. As shown in FIG. 9, the opening 526 is configured to be substantially asymmetric about a plane parallel to a longitudinal axis $A_4$ of the transmission member 520. In this manner, the flexural stiffness of the transmission member 520 can be further varied along a length of the opening 526 according to the cross-sectional shape of the transmission member 520 at a given position. More specifically, by defining an asymmetrical opening 526, the cross-sectional shape of the transmission member 520 can be selectively varied along the length of the opening 526. Furthermore, because the area moment of inertia is dependent on the cross-sectional shape, the area moment of inertia is also selectively varied along the length of the opening 526.

Figure 10:
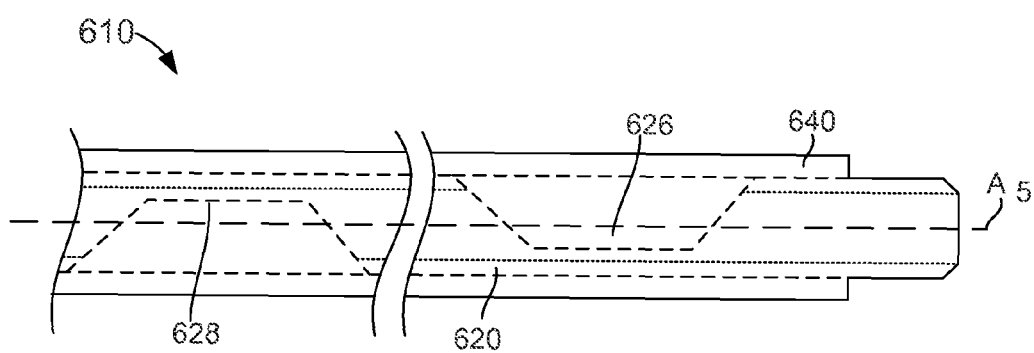
FIG. 10 is a schematic illustration of a probe assembly according to an embodiment.

While the probe assembly 510 is shown in FIG. 9 as having a transmission member 520 defining a single opening 526, in some embodiments, a transmission member can include any number of openings. For example, FIG. 10 is an illustration of a probe assembly 610, according to an embodiment. The probe assembly 610 includes a transmission member 620, defining a first opening 626 and a second opening 628, and an outer member 640. Portions of the transmission member 620 and the outer member 640 can be substantially similar in form and function to portions of the transmission member 520 and the outer member 540, respectively, described above with reference to FIG. 9. Thus, the portions of transmission member 620 and the outer member 640 are not described in further detail herein.

The transmission member 620 differs from the transmission member 420 and the transmission member 520, however, by including the first opening 626 and the second opening 628. In some embodiments, the first opening 626 and the second opening 628 can be substantially similar in shape, size, and/or configuration. In other embodiments, the first opening 626 can be, for example, symmetric about a plane perpendicular to a longitudinal axis $A_5$ of the transmission member 620 while the second opening 628 can be, for example, asymmetric about a plane perpendicular to the longitudinal axis $A_5$ (or vice versa). The first opening 626 can be arranged at any spatial orientation relative to the second opening 628. For example, while shown in FIG. 10 and being disposed on opposite sides of the transmission member 620, in some embodiments, the first opening 626 and the second opening 628 can be disposed adjacent each other on a similar side of the transmission member 620. In this manner, the first opening 626 and the second opening 628 can be selectively configured to modify the flexural stiffness of the transmission member 620. Moreover, the arrangement of the first opening 626 and the second opening 628 can be such that the first opening 626 and the second opening 628 can substantially reduce the likelihood of the transmission member 620 kinking during bending.

Figure 11:
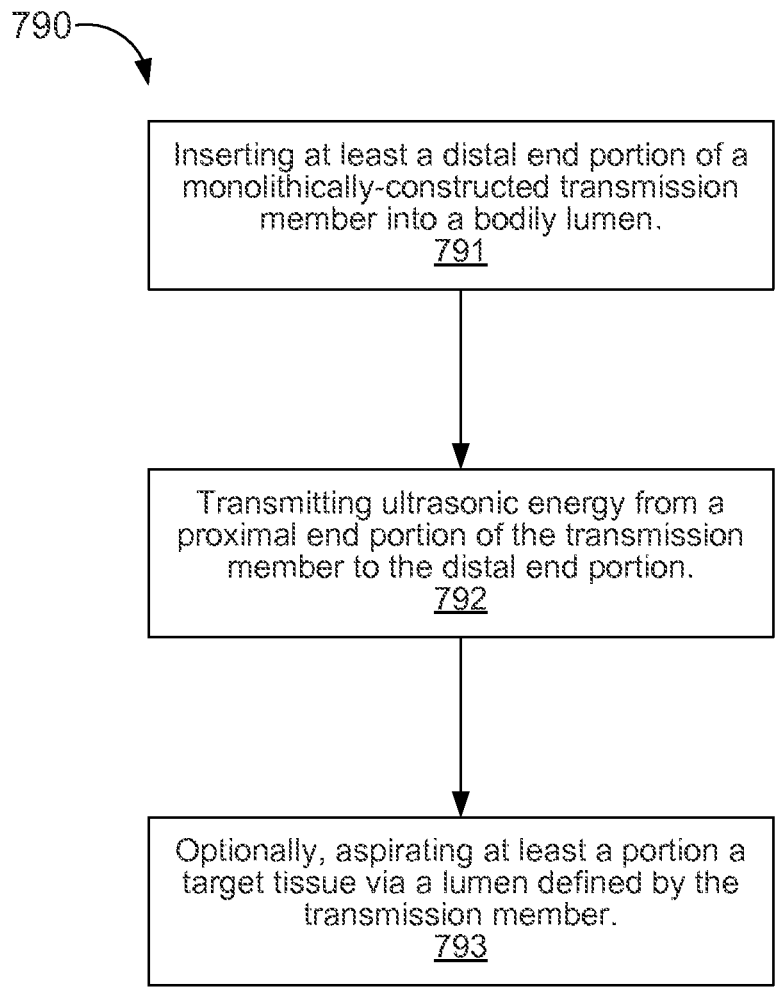
FIG. 11 is a flowchart illustrating a method for transferring ultrasonic energy to a bodily tissue.

Referring now to FIG. 11, a flowchart illustrates a method 790 for transferring ultrasonic energy to a target tissue within a body of a patient, according to an embodiment. In some embodiments, the method 790 includes inserting at least a distal end portion of a monolithically-constructed transmission member into a bodily lumen, at 791. In some embodiments, the transmission member can include a flexible portion disposed between a proximal end portion and a distal end portion that has an area moment of inertia less than an area moment of inertia of the proximal end portion and/or an area moment of inertia of the distal end portion. For example, in some embodiments, the transmission member can be substantially similar to any of the transmission members described above (e.g., the transmission member 320 described above with reference to FIGS. 4-6). In this manner, the transmission member can include an opening (e.g., similar to the transmission member 320) or multiple openings (e.g., similar to the transmission member 620) disposed along the transmission member such that the cross-sectional shape of the transmission member is changed (e.g., a cross-sectional area of the transmission member is reduced at a position along the opening), thereby decreasing a flexural stiffness of the transmission member. Moreover, in some embodiments, at least a portion of the transmission member can be disposed within an outer member configured to substantially circumscribe at least a portion of the transmission member (e.g., as described above with reference to FIGS. 7 and 8).

The method 790 includes transmitting ultrasonic energy from the proximal end portion of the transmission member to the distal end portion of the transmission member, at 792. For example, in some embodiments, the proximal end portion of the transmission member can be operably coupled to an ultrasonic energy source such that the ultrasonic energy source supplies the ultrasonic energy to the transmission member. Moreover, the distal end portion (e.g., at least a distal tip) of the transmission member can be disposed adjacent a target tissue within the body of the patient. In this manner, the transmission member can transmit at least a portion of the ultrasonic energy to the target tissue.

In some embodiments, the method 790 can optionally include aspirating at least a portion of the target tissue via a lumen defined by the transmission member, at 793. For example, in some embodiments, the transmission member can define a lumen configured to extend through the proximal end portion and the distal end portion of the transmission member. Furthermore, in embodiments in which the transmission member defines an elongate opening, the outer member disposed about the transmission member can be configured to fluidically isolate the lumen from a volume outside of the outer member. Thus, a negative pressure can be applied to the proximal end portion of the transmission member such that a portion of the target tissue (e.g., a portion of the target tissue that is broken apart by ultrasonic energy) can be aspirated through the lumen defined by the transmission member.

The embodiments and/or components described herein can be packaged independently or any portion of the embodiments can be packaged together as a kit. For example, in some embodiments, a kit can include an ultrasonic transducer assembly (e.g., such as the ultrasonic transducer assembly 150 described above with reference to FIG. 2) and any suitable number of transmission members (e.g., such as the various embodiments described above with reference to FIGS. 3-11). The transmission members included in the kit can each define a given flexural stiffness that can be different from the flexural stiffness of the other transmission members included in the kit. For example, in some embodiments, each of the transmission members included in the kit can be substantially similar in size and shape as the other transmission members included in the kit but each transmission member can each define a flexural stiffness that is substantially unique to the specific transmission member. Expanding further, in some embodiments, at least one transmission member in the kit can include an opening along a length of the transmission member that substantially reduces an area moment of inertia of the transmission member along the length of the opening. In this manner, one or more transmission members can define an opening of unique shape, size, or configuration such that each transmission member defines a unique flexural stiffness.

In some embodiments, a kit can include an ultrasonic generator similar to the ultrasonic generator 180 shown and described above. The ultrasonic generator can be configured to distinguish each transmission member contained within the kit, and can automatically adjust the electronic signal produced and/or conveyed to the ultrasonic transducer assembly to correspond to the transmission member coupled thereto. For example, because transmission members defining different levels of flexural stiffness may also have different natural (or resonant) frequencies, in such embodiments, the ultrasonic generator can adjust the frequency of the electronic signal produced to correspond to the natural frequency of the transmission member that is coupled to the ultrasonic transducer assembly.

The processor included in any of the ultrasonic generators can be a general-purpose processor (e.g., a central processing unit (CPU)) or other processor configured to execute one or more instructions stored in the memory. In some embodiments, the processor can alternatively be an application-specific integrated circuit (ASIC) or a field programmable gate array (FPGA). The processor can be configured to execute specific modules and/or sub-modules that can be, for example, hardware modules, software modules stored in the memory and executed in the processor, and/or any combination thereof. The memory included in the ultrasonic generator 180 can be, for example, flash memory, one time programmable memory, a random access memory (RAM), a memory buffer, a hard drive, a read-only memory (ROM), an erasable programmable read-only memory (EPROM), and/or so forth. In some embodiments, the memory includes a set of instructions to cause the processor to execute modules, processes and/or functions used to generate, control, amplify, and/or transfer electric current to another portion of the system, for example, the transducer assembly 150.

Some embodiments described herein, such as, for example, embodiments related to the ultrasonic generators described above, relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

The ultrasonic transmission members described herein can be fabricated and/or produced using any suitable methods. In some embodiments a transmission member can be formed via one of more manufacturing process. For example, in some embodiments, a transmission member can be formed via a tube drawing (e.g., drawn through a progressively smaller die (an extrusion process). In embodiments wherein the transmission member defines an elongate opening (e.g., the transmission member 320 described above), the opening can be formed via water jet cutting, laser cutting, machining (e.g., milling, turning, shearing, etc.). Expanding further, in some embodiments it can be desirable to form an opening along a length of a transmission member via a water jet process because such processes do not produce a heat-affected zone. Thus, the elastic modulus of the material (e.g., stainless steel or the like) that forms the transmission member is not changed. Conversely, in some embodiments it can be desirable to form an opening along a length of a transmission member via a laser cutting process because such processes produce a heat-affected zone. In such embodiments, the heating of the heat-affected zone of the transmission member due to the laser cutting of the opening can have a similar affect as tempering, thus, the stiffness of the material in a region within the heat-affected zone (e.g., along or adjacent to the opening) can be reduced.

Although certain transmission members (e.g., transmission member 320) are described above as being monolithically constructed, in other embodiments, any of the transmission members described herein can be constructed from two or more separately constructed components that are later joined together.

While the flexural stiffness of transmission members described above is spatially varied by altering the size or shape of the transmission member, in alternate embodiments, manufacturing techniques can be used to spatially vary of the flexural stiffness a transmission member while maintaining a uniform cross-sectional shape. For example, in some embodiments, a portion of a transmission member (e.g., the third portion 222 of the transmission member 220) can be heat-treated such that the elastic modulus of the portion of the transmission member is changed relative to the elastic modulus of a portion not heat treated. For example, in some embodiments, a portion of a transmission member can be tempered. In other embodiments, a transmission member in its entirety can be variably heat treated. For example, in some embodiments, a first portion can be tempered at a first temperature and a second portion can be tempered at a second temperature, different form the first. In this manner, the flexibility of the first portion and the flexibility of the second portion can be varied according to the temperature of tempering.

Figure 12:
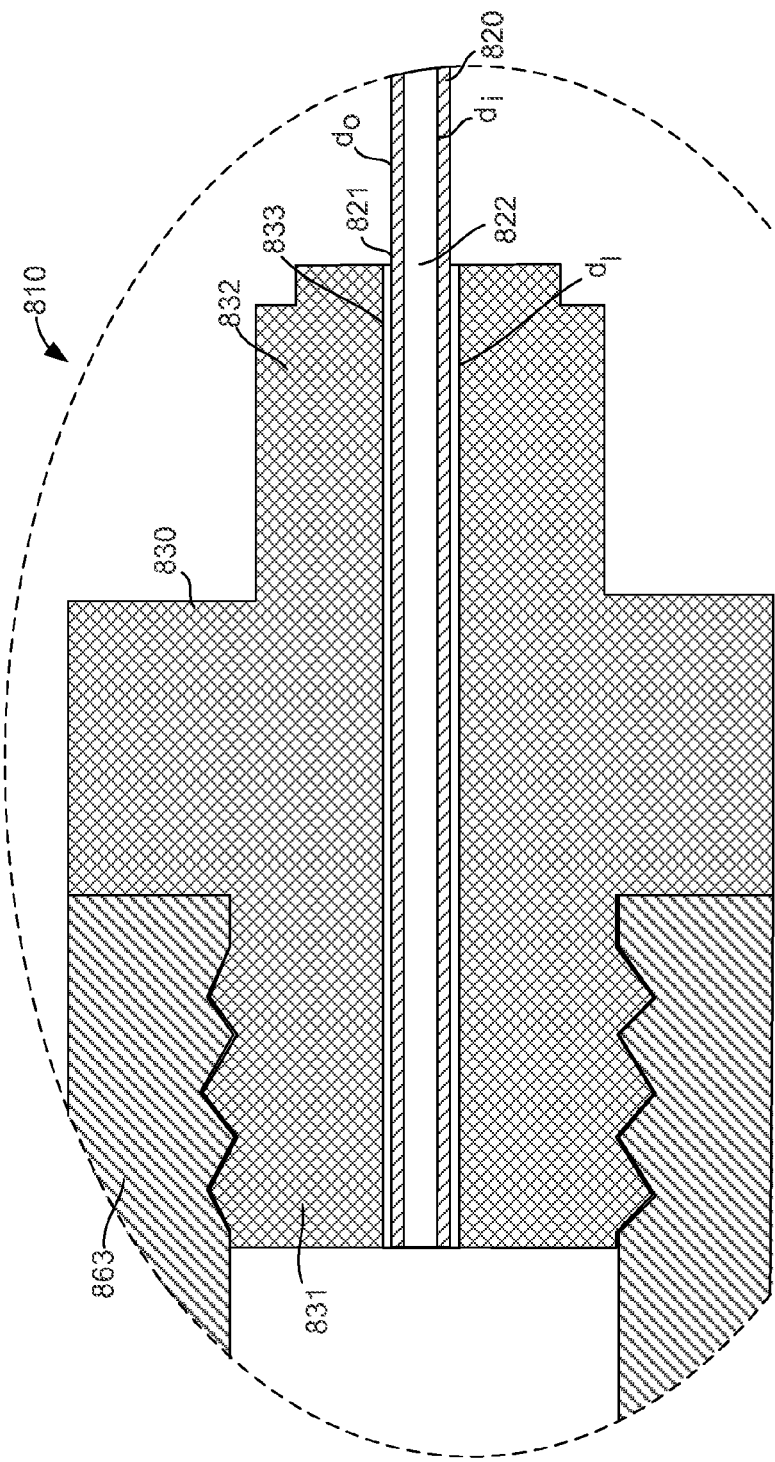
FIG. 12 is an enlarged view of a portion of a probe assembly according to an embodiment coupled to a transducer horn.

The proximal end portion of any of the transmission members described herein can be coupled to the coupler member (e.g., the coupler member 130) using any suitable mechanism. For example, as shown in FIG. 12, a probe assembly 810 can include at least a transmission member 820 and a coupler 830. The transmission member 820 and the coupler 830 can be substantially similar to the transmission member 120 and the coupler 130 described above with reference to FIGS. 1 and 2, thus, some portions of the transmission member 820 and the coupler 830 are not described in further detail herein. As shown, the coupler 830 includes a proximal end portion 831 and a distal end portion 832 and defines a lumen 833 therethrough. The proximal end portion 831 is configured to form a threaded coupling with a transducer horn 863, as described above in detail with reference to FIG. 2. The lumen 833 has a diameter $d_1$ that can be any suitable size. In this manner, the coupler 830 can be configured to receive (within the lumen 833) a portion of the transmission member 820, as described in further detail herein.

The transmission member 820 includes a proximal end portion 821 and a distal end portion (not shown in FIG. 12) and defines a lumen 822 therethrough. The transmission member 820 can be any suitable shape, size, or configuration. For example, in some embodiments, at least a portion of the transmission member 820 is substantially annular and includes an outer diameter $d_o$ and an inner diameter $d_i$. In some embodiments, the size and shape of the transmission member 820 (e.g., the outer diameter $d_o$) can substantially correspond to the size and shape (e.g., the diameter $d_1$) of the lumen 833 defined by the coupler 830 such that the proximal end portion 821 of the transmission member 820 can be disposed therein.

For example, in some embodiments, the diameter $d_1$ of the lumen 833 can be greater than the outer diameter $d_o$ of the transmission member 830, thus, the transmission member 820 can be disposed within the lumen 833 of the coupler 830. Furthermore, with the diameter $d_1$ of the lumen 833 greater than the outer diameter $d_o$ of the transmission member 820 an adhesive can be disposed within a void between the transmission member 820 and the inner surface of the coupler 830. Thus, the transmission member 820 can be fixedly coupled to the coupler 830 without the need for crimping, applying a compressive force to the transmission member or the like. Expanding further, the transmission member 820 can be fixedly coupled to the coupler 830 without plastically (e.g., permanently) deforming the transmission member, thereby decreasing the likelihood of failure and also decreasing losses due to reflections of ultrasonic energy produced by discontinuity. In other embodiments, the transmission member 120 can be coupled via welding or brazing while still realizing the benefits described above.

The transmission members described herein can be any suitable size. For example, in some embodiments, a transmission member (e.g., the transmission member 820) can have an outer diameter $d_o$ that is approximately 0.032 inches and an inner diameter $d_i$ that is approximately 0.020 inches. In this manner, the transmission member 820 can have a wall thickness of approximately 0.006 inches. In other embodiments, the outer diameter $d_o$ of the transmission member 820 can be between approximately 0.014 to 0.050 inches and the inner diameter $d_i$ can be between approximately 0.010 to 0.040 inches.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. While the embodiments have been particularly shown and described, it will be understood that various changes in form and details may be made.

For example, although the transmission member 320 is shown and described as defining an elongate opening that is substantially linear along the longitudinal axis $A_2$, in other embodiments, a transmission member can define an elongate opening that is helical and/or spiraled about the longitudinal axis. In this manner, the area moment of inertia of the region of the transmission member that defines the elongated opening can be more uniform about the longitudinal axis.

Although the transducer assembly 150 is shown in FIG. 2 as including two insulators 161 and two piezoelectric rings 162, in other embodiments, a transducer assembly can include any suitable number of insulators 161 and/or piezoelectric rings 162 in any suitable arrangement. Moreover, the insulators 161 can be formed from any suitable insulating material, ceramic materials (e.g., polyamide, expanded polytetraflouroethylene (EPTFE), or the like). Similarly, the piezoelectric rings 162 can be any suitable piezoelectric material (e.g., lead zirkonate titanate (PZT-5), PZT-8, lead titanate (PT), lead metaniobate ($PbNbO_6$), polyvinylidenefluoride (PVDF), or the like).

Although various embodiments have been described as having particular features and/or combinations of components, other embodiments are possible having a combination of any features and/or components from any of embodiments where appropriate. For example, in some embodiments, a transmission member can be a monolithically-constructed member as described with respect to the transmission member 320, and can also include an outer member coupled thereto, as described above with respect to the transmission member 420.

What is claimed is:
1. An apparatus, comprising:
a monolithically-constructed transmission member defining a lumen along a longitudinal axis of the transmission member, the transmission member including a first portion, a second portion, and a third portion, the first portion configured to be coupled to an ultrasonic energy source, the second portion including a distal tip configured to be disposed within a body, the distal tip configured to move in response to an ultrasonic energy produced by the ultrasonic energy source to transfer the ultrasonic energy from the first portion through the second portion and into a bodily tissue, the third portion disposed between the first portion and the second portion, the second portion defining a distal end open- ing in fluid communication with the lumen, the first portion and the second portion having a constant outer diameter, the third portion defining a cross-sectional area moment of inertia that is less than at least one of a cross-sectional area moment of inertia of the first portion or a cross-sectional area moment of inertia of the second portion, a sidewall of the third portion of the transmission member defining an elongated opening therethrough in fluid communication with the lumen, the elongated opening having a depth at least half as large as an outer diameter of the first portion of the transmission member; and an outer member fixedly coupled to the transmission member about the elongated opening.

2. The apparatus of claim 1, wherein:
the outer member is fixedly coupled to the transmission member via an adhesive such that the lumen is fluidically isolated from a region outside of the outer member.

3. The apparatus of claim 1, wherein a cross-sectional shape of the third portion of the transmission member is different than at least one of a cross-sectional shape of the first portion or a cross-sectional shape of the second portion.

4. The apparatus of claim 1, wherein a cross-sectional shape of the sidewall defining the elongated opening is an arc.

5. The apparatus of claim 1, further comprising:
a fitting coupled to the first portion of the transmission member, the fitting configured to couple the transmission member to the ultrasonic energy source.

6. The apparatus of claim 1, wherein a length of the elongated opening is greater than five times a diameter of the transmission member.

7. The apparatus of claim 1, wherein a cross-sectional shape of the sidewall defining the elongated opening is an arc having a subtended angle of between approximately 20 degrees and approximately 120 degrees.

8. An apparatus, comprising:
a monolithically-constructed transmission member defining a lumen along a longitudinal axis of the transmission member, the transmission member including a first portion, a second portion, and a third portion, the first portion configured to be coupled to an ultrasonic energy source, the second portion including a distal tip configured to be disposed within a body, the distal tip configured to move in response to an ultrasonic energy produced by the ultrasonic energy source to transfer the ultrasonic energy from the first portion through the second portion and into a bodily tissue, the third portion disposed between the first portion and the second portion, the first portion and the second portion having a constant outer diameter, the third portion defining a cross-sectional area moment of inertia that is less than at least one of a cross-sectional area moment of inertia of the first portion or a cross-sectional area moment of inertia of the second portion, a sidewall of the third portion of the transmission member defining an elongated opening therethrough in fluid communication with the lumen, the elongated opening having a depth at least half as large as an outer diameter of the first portion of the transmission member, the sidewall defining the elongated opening forming an arc having a subtended angle of between approximately 20 degrees and approximately 120 degrees, a cross-sectional shape of the first portion being the same as a cross-sectional shape of the second portion.

9. The apparatus of claim 8, wherein at least one of the first portion or the second portion has an inner diameter that is smaller than an inner diameter of the third portion.

10. The apparatus of claim 8, further comprising:
an outer member fixedly coupled to the transmission member via an adhesive.

11. The apparatus of claim 10, wherein an outer diameter of the outer member is constant from a proximal end portion of the outer member to a distal end portion of the outer member.

12. The apparatus of claim 8, wherein a length of the elongated opening is greater than five times a diameter of the transmission member.

13. The apparatus of claim 8, wherein the elongated opening is one of a plurality of elongated openings defined by the sidewall.

14. A method, comprising:
inserting at least a distal end portion of a monolithically-constructed transmission member into a bodily lumen, the transmission member defining a lumen along a longitudinal axis of the transmission member, the transmission member including a proximal end portion and a flexible portion disposed between the proximal end portion and the distal end portion, the proximal end portion and the distal end portion having a constant outer diameter, the flexible portion defining a cross-sectional area moment of inertia that is less than at least one of a cross-sectional area moment of inertia of the proximal end portion or a cross-sectional area moment of inertia of the distal end portion, the distal end portion defining a distal end opening in fluid communication with the lumen defined by the transmission member, a sidewall of the flexible portion of the transmission member defining an elongated opening therethrough in fluid communication with the lumen defined by the transmission member, the elongated opening having a depth at least half as large as an outer diameter of the proximal end portion of the transmission member, an outer member coupled to the transmission member about the elongated opening to prevent fluid communication between the lumen and a region outside of the outer member via the elongated opening;

transmitting an ultrasonic energy from the proximal end portion through the flexible portion and the distal end portion such that a portion of the ultrasonic energy is delivered to a target tissue within the bodily lumen; and aspirating at least a portion of the target tissue via the distal end opening and the lumen defined by the transmission member.

15. The method of claim 14, wherein the outer member is fixedly coupled to the transmission member via an adhesive.

16. An apparatus, comprising:
a monolithically-constructed transmission member defining a lumen along a longitudinal axis of the transmission member, the transmission member including a first portion, a second portion, and a third portion, the first portion configured to be coupled to an ultrasonic energy source, the second portion configured to be disposed within a body to transfer an ultrasonic energy from the first portion into a bodily tissue, the third portion disposed between the first portion and the second portion, the second portion defining a distal end opening in fluid communication with the lumen, the first portion and the second portion having a constant outer diameter, the third portion defining a cross-sectional area moment of inertia that is less than at least one of a cross-sectional area moment of inertia of the first portion or a cross-sectional area moment of inertia of the second portion, a sidewall of the third portion of the transmission member defining an elongated opening therethrough in fluid communication with the lumen, the elongated opening having a depth at least half as large as an outer diameter of the first portion of the transmission member, a length of the elongated opening being between 40 percent and 90 percent of a length of the transmission member.

17. The apparatus of claim 16, further comprising:
an outer member fixedly coupled to the transmission member.

18. The apparatus of claim 16, further comprising:
an outer member fixedly coupled to the transmission member via an adhesive, a portion of the outer member disposed about the elongated opening such that the lumen is fluidically isolated from a region outside of the outer member.

19. The apparatus of claim 16, wherein a cross-sectional shape of the sidewall defining the elongated opening is an arc.

20. The apparatus of claim 16, further comprising:
a fitting coupled to the first portion of the transmission member, the fitting configured to couple the transmission member to the ultrasonic energy source.

\* \* \* \* \*